(12) United States Patent
Cargill et al.

(10) Patent No.: US 9,689,782 B2
(45) Date of Patent: Jun. 27, 2017

(54) SMALL OBJECT DISTRIBUTION AUTOMATION

(71) Applicant: Monsanto Technology LLC, St. Louis, MO (US)

(72) Inventors: Edward J. Cargill, Cottleville, MO (US); Kevin L. Deppermann, St. Charles, MO (US); Ujwal A. Deole, St. Louis, MO (US); Michael Dayawon, St. Louis, MO (US); William M. Fischer, St. Peters, MO (US); John F. Lasinski, Fenton, MO (US); Jamaine R. Hubbard, St. Louis, MO (US); Amy D. Trinchard, Cary, NC (US); Josh G. Rameaka, Durham, NC (US); Chris Tierney, Apex, NC (US); Angela R. Koestel, St. Louis, MO (US)

(73) Assignee: Monsanto Technology LLC, St. Louis, MO (US)

( * ) Notice: Subject to any disclaimer, the term of this patent is extended or adjusted under 35 U.S.C. 154(b) by 39 days.

(21) Appl. No.: 14/414,925

(22) PCT Filed: Jul. 19, 2013

(86) PCT No.: PCT/US2013/051226
  § 371 (c)(1),
  (2) Date: Jan. 15, 2015

(87) PCT Pub. No.: WO2014/015223
  PCT Pub. Date: Jan. 23, 2014

(65) Prior Publication Data
  US 2015/0177110 A1   Jun. 25, 2015

Related U.S. Application Data

(60) Provisional application No. 61/673,524, filed on Jul. 19, 2012.

(51) Int. Cl.
  G01N 1/04   (2006.01)
  G01N 1/14   (2006.01)
  (Continued)

(52) U.S. Cl.
  CPC ............... *G01N 1/14* (2013.01); *B65B 1/16* (2013.01); *B65B 25/02* (2013.01); *B65G 47/16* (2013.01); *B65G 47/80* (2013.01)

(58) Field of Classification Search
  CPC .. G01N 1/14; B65B 25/02; B36B 1/16; B65G 47/16; B65G 47/80
  (Continued)

(56) References Cited

U.S. PATENT DOCUMENTS 2,398,234 A   4/1946   Long
4,228,864 A   10/1980   Berger et al.
(Continued)

OTHER PUBLICATIONS

International Search Report from corresponding PCT/US2013/051226 mailed Jan. 31, 2014.

*Primary Examiner* — Charles A. Fox
*Assistant Examiner* — James Buckle, Jr.
(74) *Attorney, Agent, or Firm* — Polster Lieder

(57) ABSTRACT

An automated small particle distribution system is provided for transferring small particles from source tubes to destination tubes. The system includes a loading deck that is structured and operable to store and provide a plurality of source tube trays and a plurality of destination tube trays. Each source tube tray includes a plurality of source tubes stored therein, and each destination tube tray includes a plurality of destination tubes stored therein. The system additionally includes a work deck is structured and operable to receive selected source tube trays and selected destination tube trays from the loading deck, aspirate various specified amounts of small objects stored in selected source tubes, and
(Continued)

deposit the aspirated small objects into selected destination tubes without cross-contamination of small objects.

16 Claims, 16 Drawing Sheets

(51) Int. Cl.
*B65B 25/02* (2006.01)
*B65B 1/16* (2006.01)
*B65G 47/16* (2006.01)
*B65G 47/80* (2006.01)

(58) Field of Classification Search
USPC .................................................. 414/331.02
See application file for complete search history.

(56) References Cited

U.S. PATENT DOCUMENTS

| | | | |
|---|---|---|---|
| 5,721,384 A | 2/1998 | Tanihata | |
| 6,150,158 A | 11/2000 | Bhide et al. | |
| 6,705,827 B2 | 3/2004 | Keller et al. | |
| 7,533,493 B2 * | 5/2009 | Brusatore | A01G 31/047 47/59 R |
| 7,818,917 B2 * | 10/2010 | Brusatore | A01G 31/047 47/59 R |
| 7,975,632 B2 | 7/2011 | Gogerty et al. | |
| 7,998,669 B2 | 8/2011 | Deppermann et al. | |
| 8,189,901 B2 * | 5/2012 | Modiano | B07C 5/34 250/339.07 |
| 8,833,565 B2 * | 9/2014 | Becker | A01C 1/00 209/552 |
| 8,863,436 B2 * | 10/2014 | Becker | G01N 1/04 47/14 |
| 2006/0042527 A1 * | 3/2006 | Deppermann | A01C 1/025 111/171 |
| 2006/0230674 A1 * | 10/2006 | Marchildon | A01G 31/047 47/60 |
| 2007/0172396 A1 | 7/2007 | Neeper et al. | |
| 2007/0251145 A1 * | 11/2007 | Brusatore | A01G 31/047 47/83 |
| 2008/0000815 A1 * | 1/2008 | Deppermann | B07C 5/3425 209/552 |
| 2008/0110088 A1 * | 5/2008 | Brusatore | A01G 31/047 47/79 |
| 2014/0059928 A1 * | 3/2014 | McAleer | A01G 31/047 47/65.7 |

* cited by examiner

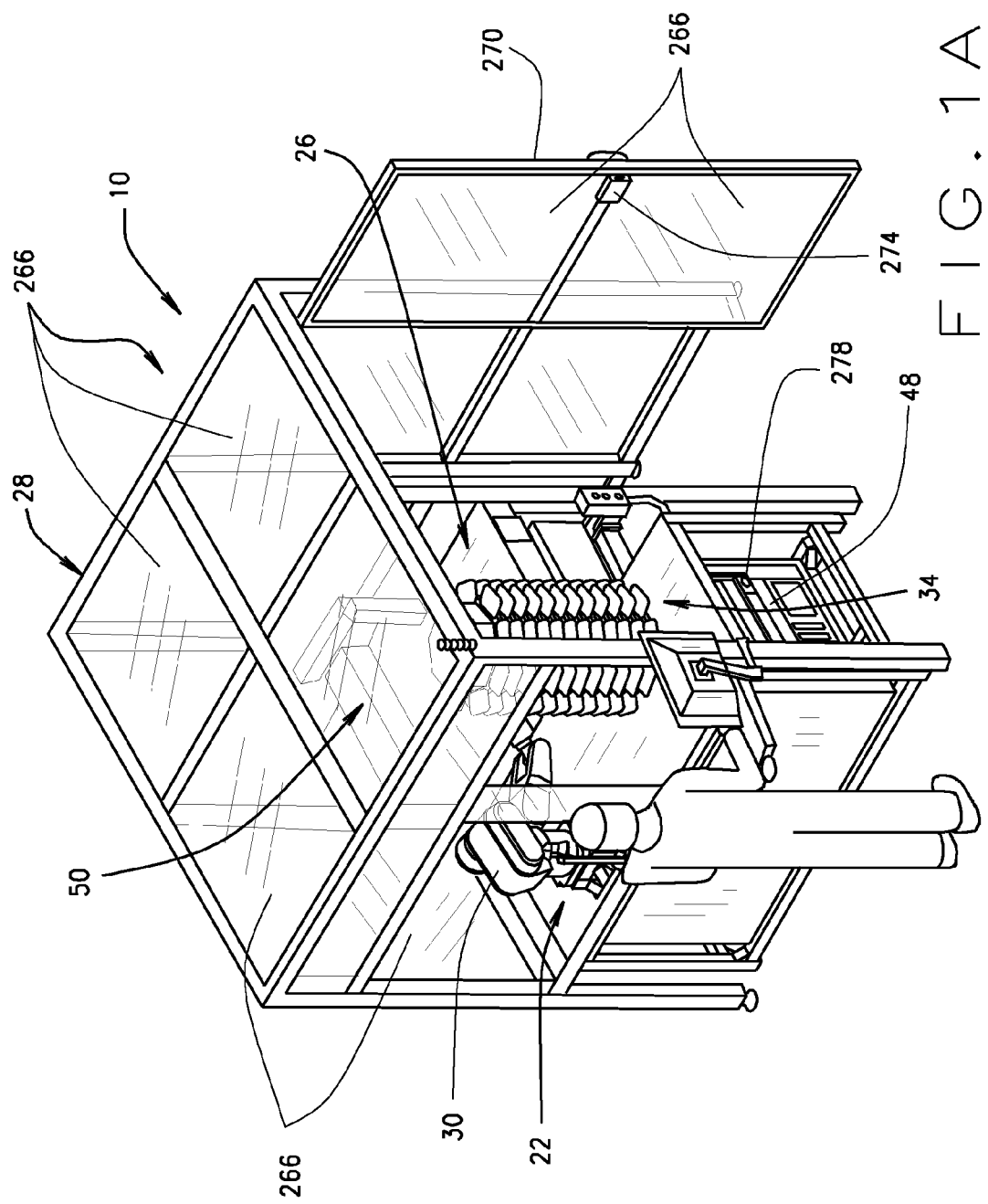

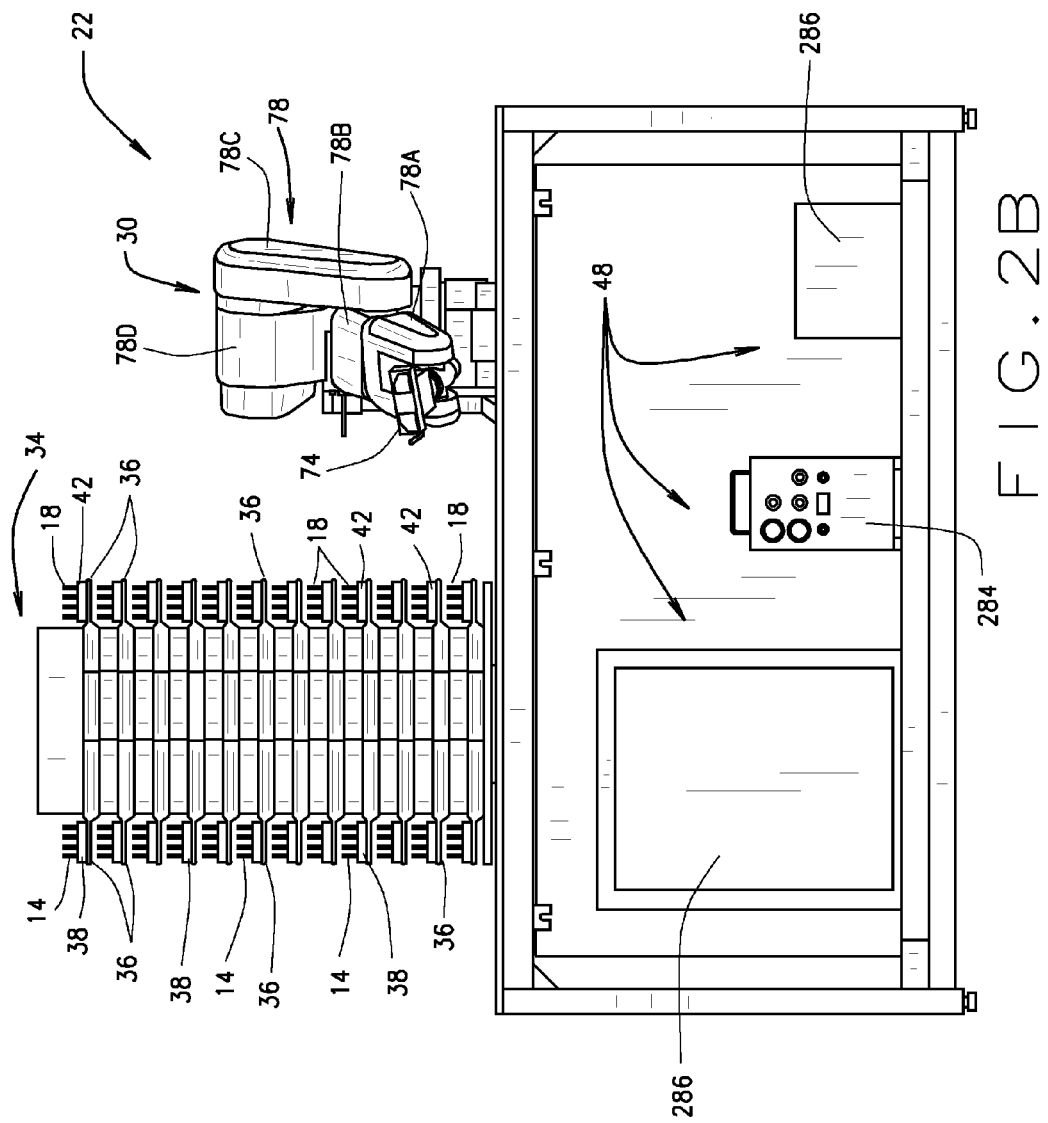

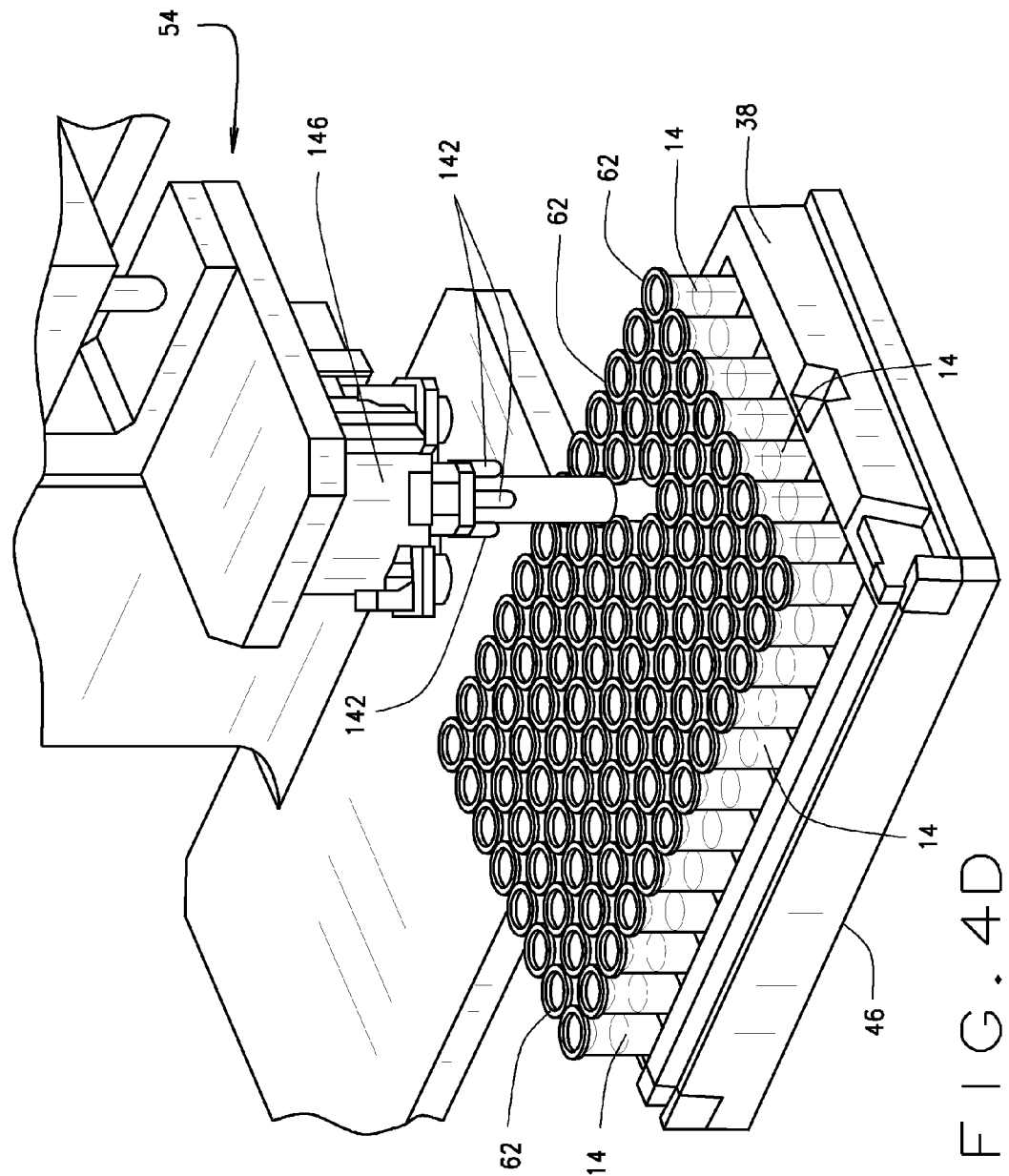

SMALL OBJECT DISTRIBUTION AUTOMATION

CROSS-REFERENCE TO RELATED APPLICATIONS

This application is the US national stage under 35 U.S.C. §371 of International Application No. PCT/US2013/051226, filed on Jul. 19, 2013, which claims the benefit of U.S. Provisional Application No. 61/673,524, filed on Jul. 19, 2012. The disclosure of the above application is incorporated herein by reference in its entirety.

FIELD

The present disclosure relates generally to automated systems and methods for distributing small objects, e.g., small seeds such as *Arabidopsis* seeds, from source containers into destination containers.

BACKGROUND

The statements in this section merely provide background information related to the present disclosure and may not constitute prior art.

The distribution, or sorting, of selected quantities of very small agricultural, manufactured or produced objects, such as very small seeds, granular products or powder, from a source container to one or more destination containers can be cumbersome, painstakingly tedious, and wrought with human error.

For example, in seed breeding, often select quantities of very small seed, e.g., *Arabidopsis* seed, must be parsed from a larger quantity of seed, whereafter the parsed seed is analyzed and/or planted for further analysis to identify various attributes of the respective seed, e.g., phenotypic and/or genotypic traits. Typically, the distribution/sorting process is painstakingly performed by hand, which is extremely time consuming and subject to human error.

SUMMARY

The present disclosure provides an automated small particle distribution system for transferring small particles from source tubes to destination tubes. In various embodiments the system includes a loading deck that is structured and operable to store and provide a plurality of source tube trays and a plurality of destination tube trays. Each source tube tray includes a plurality of source tubes stored therein, and each destination tube tray includes a plurality of destination tubes stored therein. In such embodiments, the system additionally includes a work deck is structured and operable to receive selected source tube trays and selected destination tube trays from the loading deck, aspirate various specified amounts of small objects stored in selected source tubes, and deposit the aspirated small objects into selected destination tubes without cross-contamination of small objects.

Further areas of applicability of the present teachings will become apparent from the description provided herein. It should be understood that the description and specific examples are intended for purposes of illustration only and are not intended to limit the scope of the present teachings.

DRAWINGS

The drawings described herein are for illustration purposes only and are not intended to limit the scope of the present teachings in any way.

FIG. 1A is an isometric view of an automated transfer and distribution system, in accordance with various embodiments of the present disclosure.

FIG. 2B is a side view of the loading deck shown in FIG. 2A, in accordance with various embodiments of the present disclosure.

FIG. 4D is an isometric view of a source tray positioned in a tray dock of the work deck shown in FIG. 3A, in accordance with various embodiments of the present disclosure.

Corresponding reference numerals indicate corresponding parts throughout the several views of drawings.

DETAILED DESCRIPTION

Figure 1B:
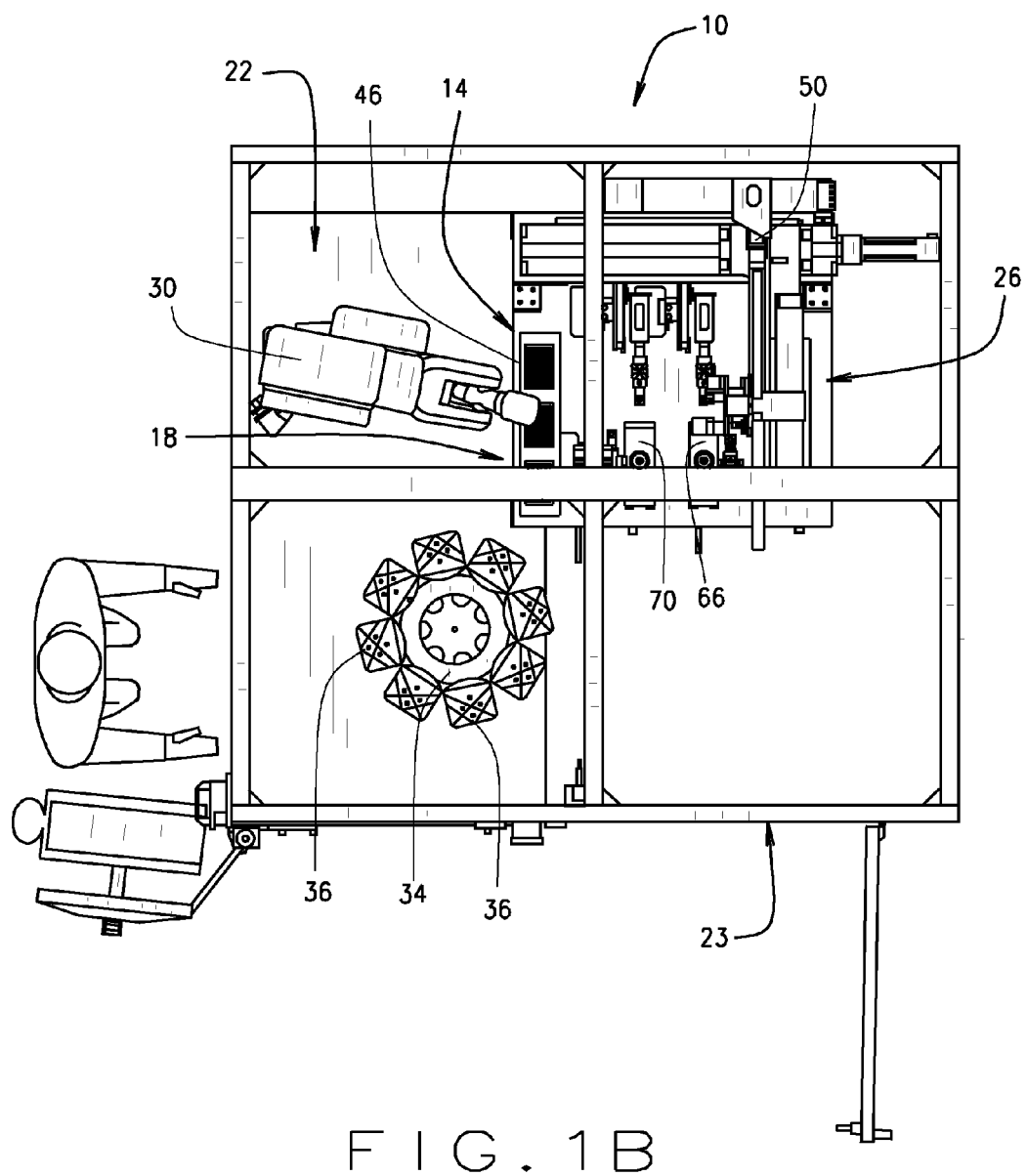
FIG. 1B is a top view of the automated transfer and distribution system shown in FIG. 1A, in accordance with various embodiments of the present disclosure.

The following description is merely exemplary in nature and is in no way intended to limit the present teachings, application, or uses. Throughout this specification, like reference numerals will be used to refer to like elements.

Referring to FIGS. 1A and 1B, the present disclosure provides an automated small particle distribution system 10 that is structured and operable to transfer small particles, e.g., seeds such as *Arabidopsis* seeds, from source tubes or containers 14 to destination tubes or containers 18. Each of the source and destination tubes 14 and 18 are pre-labeled with a 2D barcode. Each source tube 14 contains an amount of a particular sample of a particulate substance, e.g., a specific type of seed having specific genetic characteristics. Moreover, the samples in the source tubes 14 can have differences from sample to sample in volume, density, particulate size, moisture level, oil levels, etc.

Although the system 10 can be utilized to transfer any type of particulate substance, e.g., small particles, powder, crushed or ground materials, or any other particulate matter, for convenience, clarity and brevity, the system 10 will be exemplarily described herein as being utilized to automatically transfer small seeds, such as *Arabidopsis* seeds, from the source tubes 14 to the destination tubes 18.

As described further below, in various embodiments, the system 10 is further structured and operable to detect variable fill volumes in source tubes 14, replace excess seeds in the same source tube 14 from which the seeds were removed, and de-cap and re-cap the source tubes 14. An exemplary use of the system 10 can be to automate the selection and distribution of *Arabidopsis* seeds that are primarily used for screening constructs.

The system 10 comprises a loading deck 22 that is operatively connected to a work deck 26. The loading deck 22 and the work deck 26 are both totally enclosed within an environmentally and static controlled system enclosure 28. Generally, the loading deck includes a 6-axis robot arm 30 and a motorized storage carousel 34 that includes a plurality of barcode labeled tray receptacles 36 for storing barcode labeled source tube trays 38 (shown in FIG. 2B) that hold the source tubes 14 containing stock seeds, and barcode labeled destination tube trays 42 that hold the destination tubes 18 that will contain distributed seeds, post-processing. The carousel 34 can be structured and operable to hold any number of trays 38 and 42. For example, in various implementations the carousel can be structured and operable to hold up to ninety-six trays 38 and 42 (i.e., 9216 tubes 14 and 18) for processing.

Generally, the 6-axis robot arm 30 transfers trays 38 and/or 42 from the carousel 34 to one or more tray docks 46 of work deck 26 based on tray barcode identification pre-loaded into automated small particle distribution system software, i.e., one or more system control algorithms. The small particle distribution system (SPDS) software is executed by a central control system 48 of the system 10 to control all the automated operations of the system 10, as described herein. Although various operations and functionality of the system 10 are described herein as being controlled by the central control system 48, it should be understood that it is not the central control system 48 that controls the operations and functionality of system 10. But, rather it is the execution of the SPDS software by one or more processors of the central control system 48 that controls all operations and functionality of the system 10.

Figure 3A:
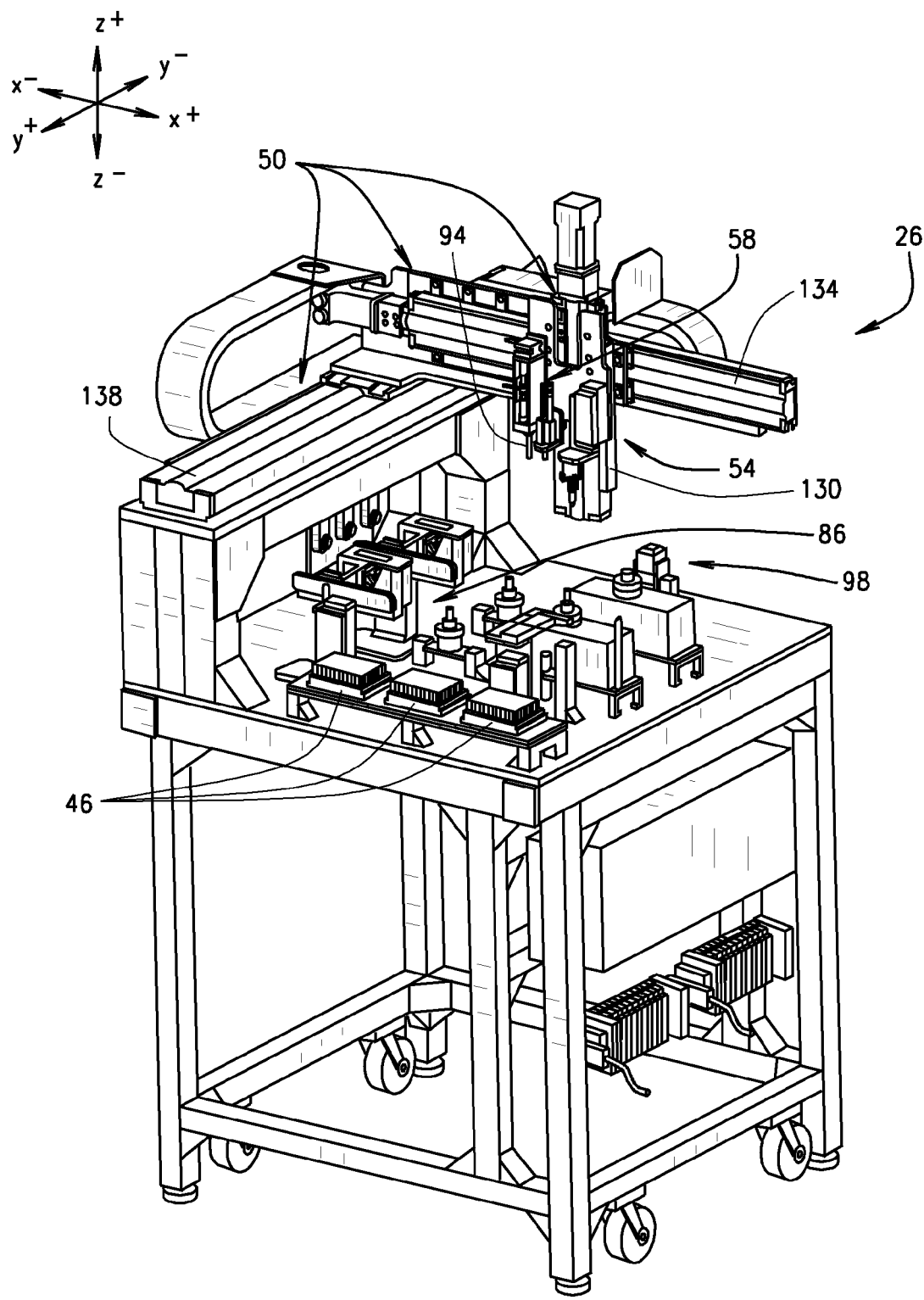
FIG. 3A is an isometric view of a work deck of the automated transfer and distribution system shown in FIGS. 1A and 1B, in accordance with various embodiments of the present disclosure.
Figure 3B:
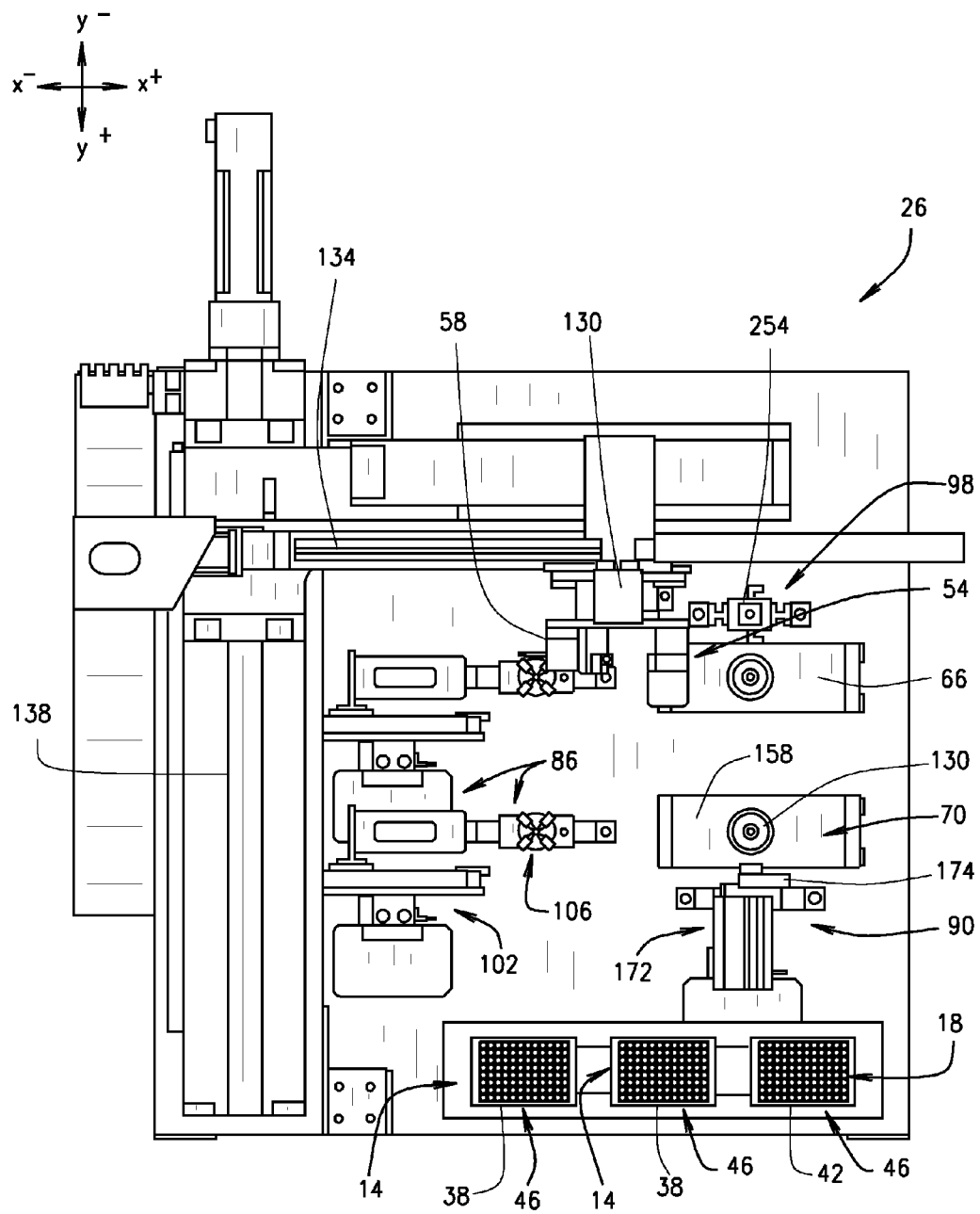
FIG. 3B is a top view of the work deck shown in FIG. 3A, in accordance with various embodiments of the present disclosure.
Figure 3C:
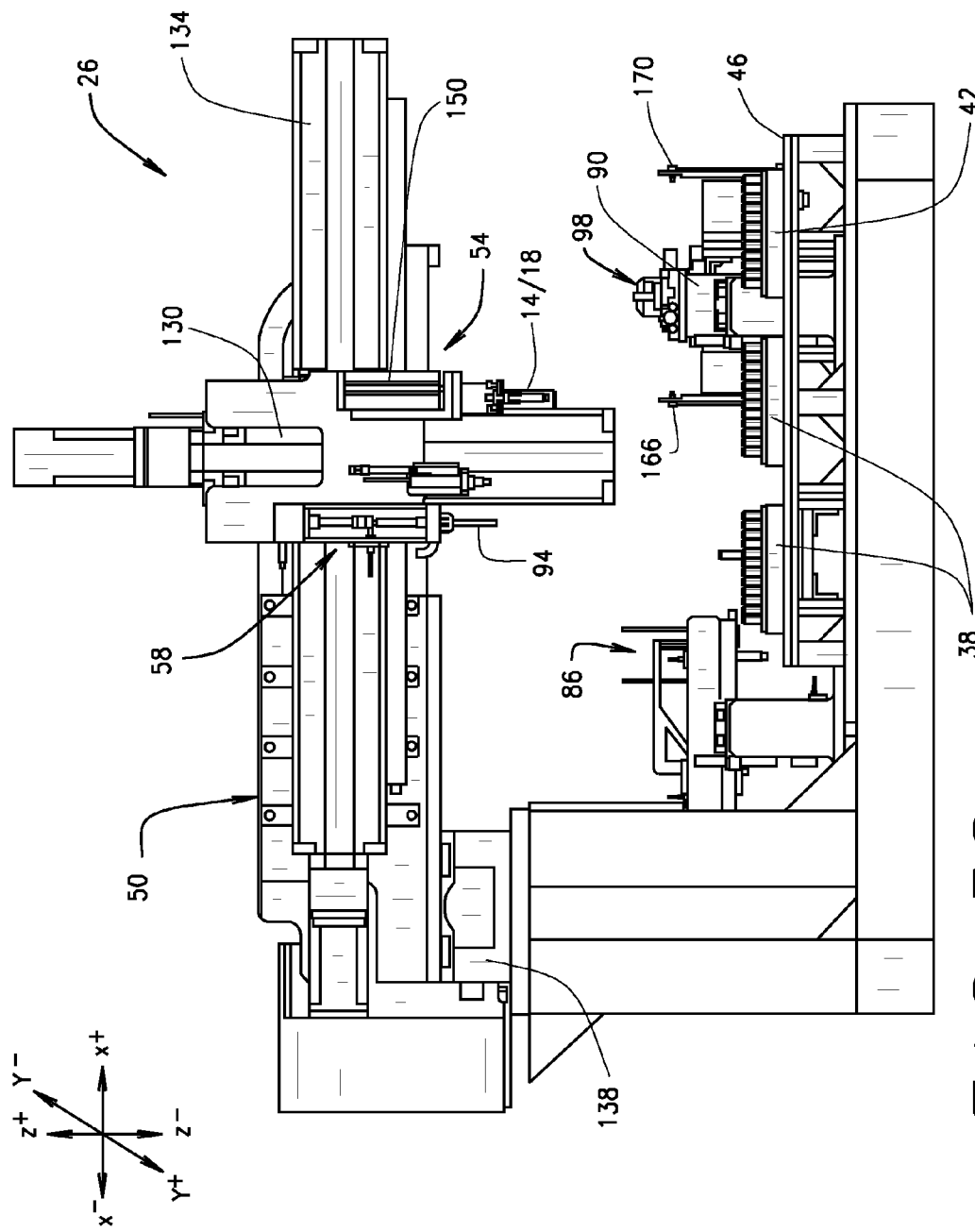
FIG. 3C is a side view of the work deck shown in FIG. 3A, in accordance with various embodiments of the present disclosure.

The work deck 26 includes a work deck XYZ-axis robot 50, which includes a tube handling device 54 (shown in FIG. 3A) for transferring the source and destination tubes 14 and 18 to and from the respective source and destination trays 38 and 42 located in the tray docks 46. The work deck XYZ-axis robot 50 additionally includes an automated volume adjustable pipette 58 (shown in FIG. 3A) that is structured and operable to aspirate, i.e., remove, selected amounts e.g., volumes and/or weight, of seed from the selected source tubes 14 and distribute, or dispose, the aspirated seed into a respective destination tube 18. A single source tube 14 and a single destination tube 18 are processed at the same time. For convenience and clarity, the work deck XYZ-axis robot 50 will be simply referred to herein as the work deck robot 50.

In general operation, once the selected source and destination tube trays 38 and 42 have been removed from the carousel 34 and placed in the tray docks 46, via the 6-axis robot arm 30, a selected source tube 14 is removed from the respective source tube tray 38 by the work deck robot 50, based on the source tube barcode identification that is pre-loaded into the SPDS software. Subsequently, a tube cap 62 (shown in FIG. 4E) disposed on or in the top of the respective source tube 14 is removed. As the source tube cap 62 is being removed, the word deck robot 50 selectively removes a destination tube 18 from the respective destination tube tray 42, based on the destination tube barcode identification that is pre-loaded into the SPDS software and places the selected destination tube 18 into a destination tube balance 66 of the work deck 26. Thereafter, the work deck robot 50 disposes the de-capped source tube 14 into a source tube balance 70.

Once the source and destination tubes 14 and 18 have been placed into the respective source and destination balances 70 and 66, a specified amount of seed, as designated by tables and/or databases stored in the control system 48, is extracted from the source tube 14, via cooperative operation of the pipette 58 and the work deck robot 50. Any excess seed that may be attached to the end of the pipette 58 is then automatically wiped off of the pipette 58 and allowed to fall back into the respective source tube 14. The extracted seed is then deposited into the destination tube 18, via cooperative operation of the pipette 58 and the work deck robot 50. After the seed has been extracted from the source tube 14 and deposited into the destination tube 18, the source tube 14 is removed from the source tube balance 70, re-capped and replaced in the respective source tube tray 38. Similarly, the destination tube 18 containing the deposited seed is removed from the destination tube balance 66 and replaced in the respective destination tube tray 42. Alternatively, the source tube 14 can remain within the source tube balance 70 for distribution of seed to a different destination tube 18.

Subsequently, specified amounts of other specified seed types can be similarly transferred from other selected source tubes 14 to respective destination tubes 18. Once, all the specified amounts of specified seed types from a particular source tube tray 38 have been transferred to respective destination tubes 18, the 6-axis robot arm 30 removes the respective source tube tray 38 from the tray dock 46 and replaces it in the storage carousel 34. Similarly, the destination tube tray 42 can be replaced in the storage carousel 34. Or, the destination tube tray 42 can remain positioned on the tray dock 46 until all the destination tubes 18 of the respective destination tube tray 42 have had seed deposited therein, whereafter, the 6-axis robot arm 30 will remove the respective destination tube tray 42 from the tray dock 46 and replace it in the storage carousel 34.

Figure 2A:
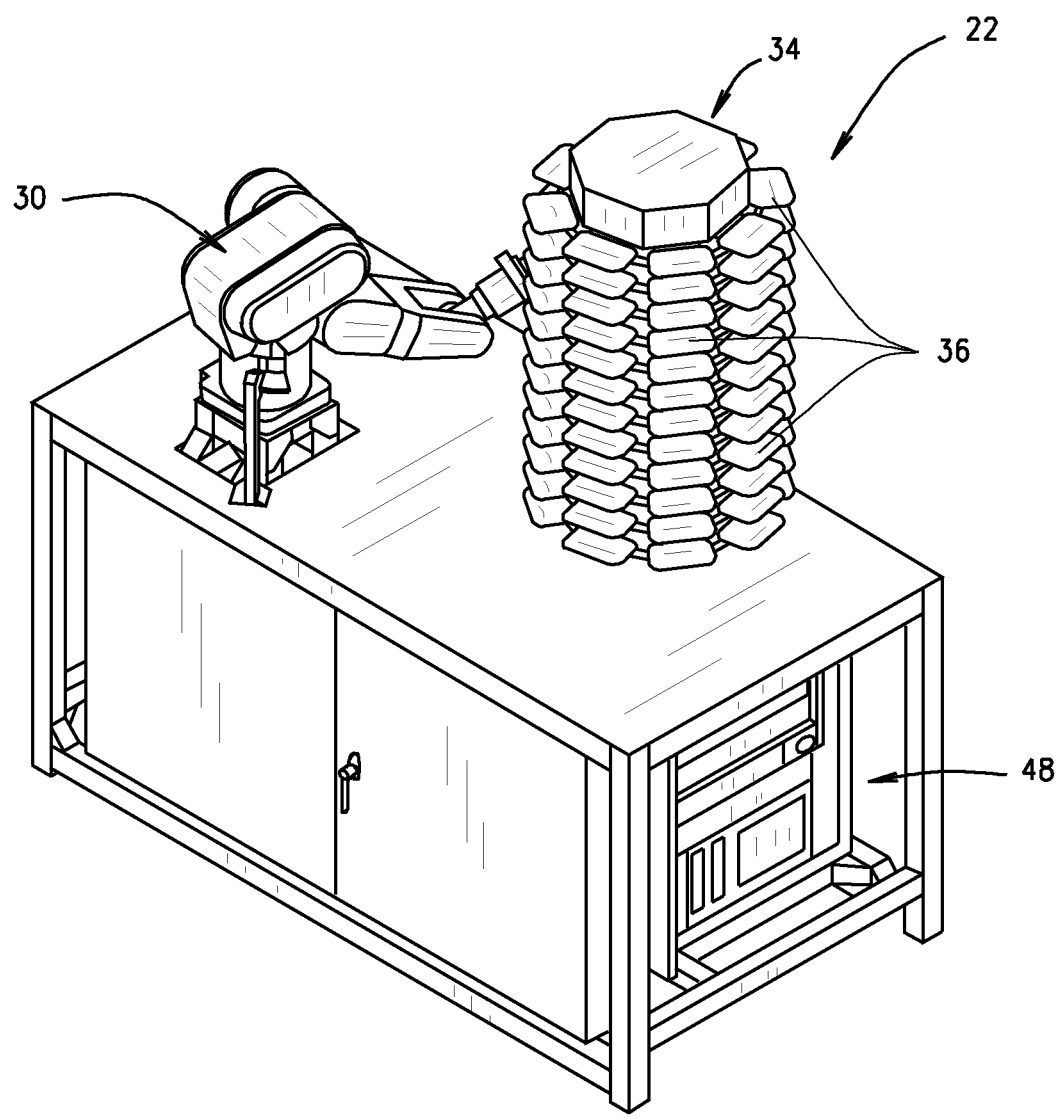
FIG. 2A is an isometric view of a loading deck of the automated transfer and distribution system shown in FIGS. 1A and 1B, in accordance with various embodiments of the present disclosure.

Referring now to FIGS. 2A and 2B, the 6-axis robot arm 30 is generally an automated 6-axis articulating arm that is controlled by the central control system 48. Generally, the 6-axis robot arm 30 comprises a hand 74 that is rotatably connected to an articulating arm 78 comprising a series of rotatably interconnected linkage arms 78A, 78B, 78C and 78D. The 6-axis robot is operable to position the hand 74 generally at a point within a spherical volume of space having radial distance equal to a length of the articulating arm 78 in a fully extended position. Additionally, the hand 74 includes a pair of fingers 82 that are structured and operable to controllably grasp and release the source and destination trays 38 and 42.

The motorized storage carousel 34 is operable to rotate about its longitudinal axis as controlled by the control system 48 to provide access to particular columns of tray receptacles 36 by the hand 74 of the 6-axis robot arm 30. Particularly, when a specific tray 38 or 42 is identified for removal from the carousel 34, the control system 48 rotates the carousel 34 to position the column of tray receptacles 36 including the specified tray 38 or 42 in a pick and place location adjacent to and accessible by the 6-axis robot arm 30. As described above, each tray 36 is barcode labeled as is each source tube tray 38 and destination tube tray 42. Accordingly, as each source tube tray 38 and destination tube tray 42 is loaded onto a respective tray receptacle 36, the corresponding tray and receptacle barcodes are associated and entered into a database or table of the control system 48, i.e., a database or table stored in one or more computer readable electronic storage devices of the control system 48.

Thus, any empty tray receptacle 36 and any source or destination tube tray 38 or 42 can be positioned in the pick and place position, via automated rotation of the storage carousel 34, whereafter the 6-axis robot can replace a post-processed source or destination tube tray 38 or 42 into the corresponding empty tray receptacle 36, or pick (i.e. remove) a specified source or destination tube tray 38 or 42 from the respective receptacle 36. As described above, the 6-axis robot arm 30 transports the picked source or destination tube trays 38 and 42 to one of the tray docks 46, as designated by the control system 48, where the trays 38 and 42 are docked. Additionally, the 6-axis robot arm 30 transports selected post-processed source or destination tube trays 38 of 42 from the respective tray dock 46 to the carousel 34, where the tray 38 or 42 is placed in (i.e., returned to) the respective empty tray receptacle 36.

Referring now to FIGS. 3A, 3B, 3C, 4A, 4B and 4C, as described above, the work deck 26 includes the tray docks 46, the work deck robot 50 comprises the tube handling device 54 and automated volume adjustable pipette 58, and the source and destination tube balances 66 and 70. The work deck 26 additionally includes a capping and decapping (C&D) station 86 for removing and replacing the tube caps 62 from the source tubes 14, a pipette wiping (PW) device 90 for removing excess seed from the tip of a pipette nozzle 94, a pipette cleaning station 98 for removing residual seed from the pipette nozzle 94 after seed is deposited into a destination tube 18, as described herein.

The C&D station 86 includes a capping and decapping station XZ-axis robot 102, referred to herein as the C&D robot 102, and a source tube clamp stand 106. The C&D robot 102 includes a cap gripper 110 for grasping tube caps 62, a C&D X-axis linear stage 114 for moving the cap gripper 110 in the X$^{+/-}$ directions and a C&D Z-axis linear stage 118 for moving the cap gripper 110 in the Z$^{+/-}$ directions. The cap gripper 110 comprises at least a pair of gripper fingers 120 that are controlled by a cap gripper actuator 121 to grasp and release the caps 62 of the source tubes 14 retained within the source tube clamp stand 106. The source tube clamp stand 106 includes a tube clamping mechanism comprising clamp fingers 122 that are controlled by a source tube clamp stand actuator 126 to clamp and release source tubes 14.

The tube handling device 54 and the pipette 58 are mounted to a work station Z-axis linear stage 130 that is operable to move the tube handling device 54 and the pipette 58 in the Z+/− directions. The work station Z-axis linear stage 130 is mounted to a work station X-axis linear stage 134 that is operable to move the work station Z-axis linear stage 130, the tube handling device 54 and the pipette 58 in the X+/− directions. The work station X-axis linear stage 134 is mounted to a work station Y-axis linear stage 138 that is operable to move the X-axis linear stage 134, the Z-axis linear stage 130, the tube handling device 54 and the pipette 58 in the Y+/− directions. The tube handling device 54 includes a tube grasping mechanism comprising grasp fingers 142 (e.g., two, three, four or more grasp fingers 142) that are controlled by a handling device actuator 146 to grasp and release source tubes 14. In various embodiments, the tube handling device 54 additionally includes a linear actuator 150 that is operable to extend and retract the tube grasping mechanism in the Z+/− directions.

In operation, via source tube barcode information stored in the control system 48, a selected capped source tube 14 is removed from a source tube tray 38 disposed in a tray dock 46 and placed in the source tube clamp stand 106 of the C&D station 86, via cooperative operation of the work deck robot 50 and the tube handling device 54. The clamp stand actuator 126 then operates the clamp fingers 122 to grasp and retain the selected source tube 14. Subsequently, cooperative operation of the C&D robot 102 and the cap gripper 110 removes the cap 62 from the selected source tube 14. The clamp stand actuator 126 operates the clamp fingers 122 to release the source tube 14 once the respective cap has been removed, whereafter the cooperative operation of work deck robot 50 and the tube handling device 54 removes the decapped source tube 14 from the clamp stand 106 and places the decapped source tube 14 into a head 154 of the source tube balance 70.

Figure 4A:
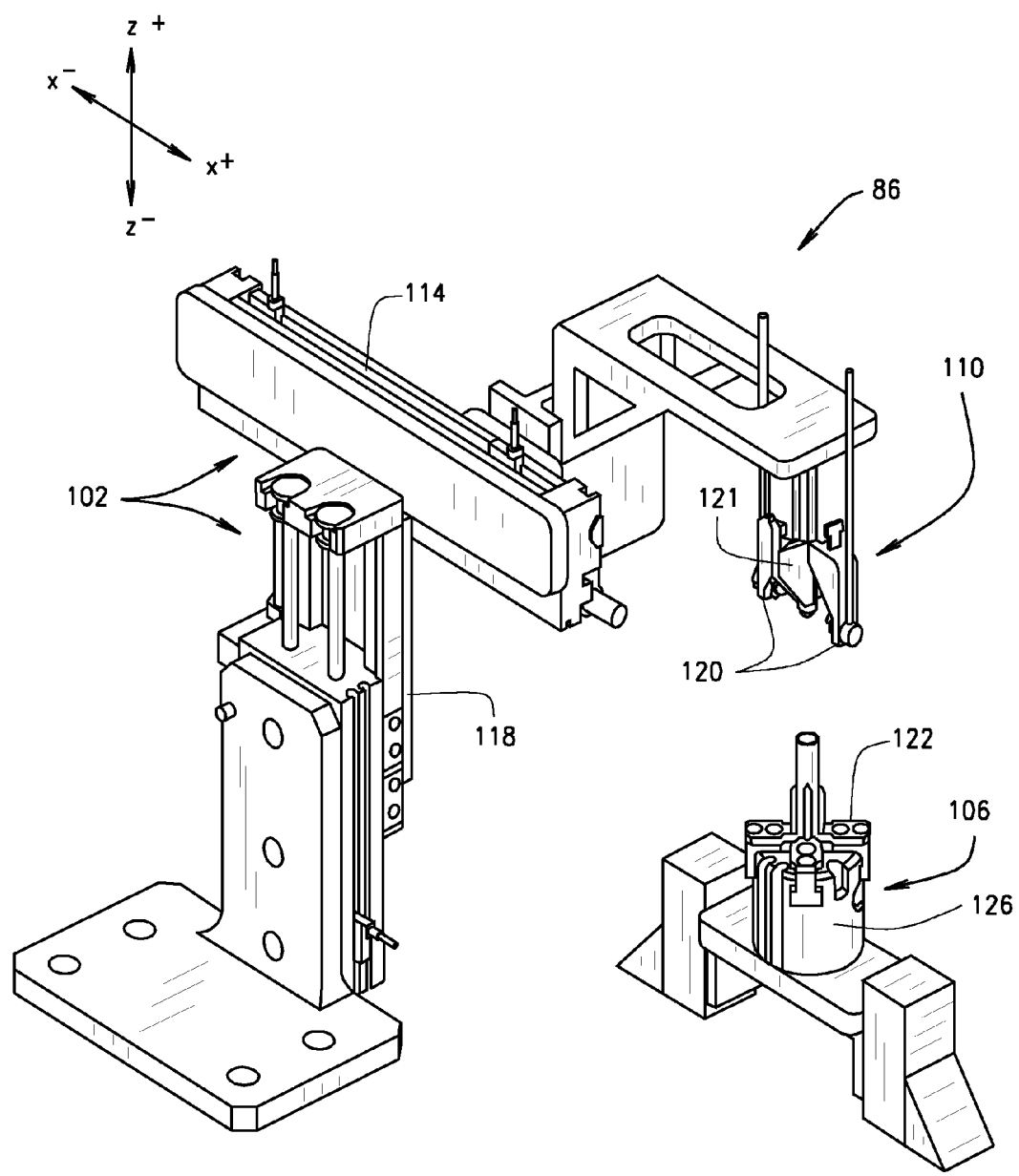
FIG. 4A is an isometric view of a capping and decapping stage of the work deck shown in FIG. 3A, in accordance with various embodiments of the present disclosure.
Figure 4B:
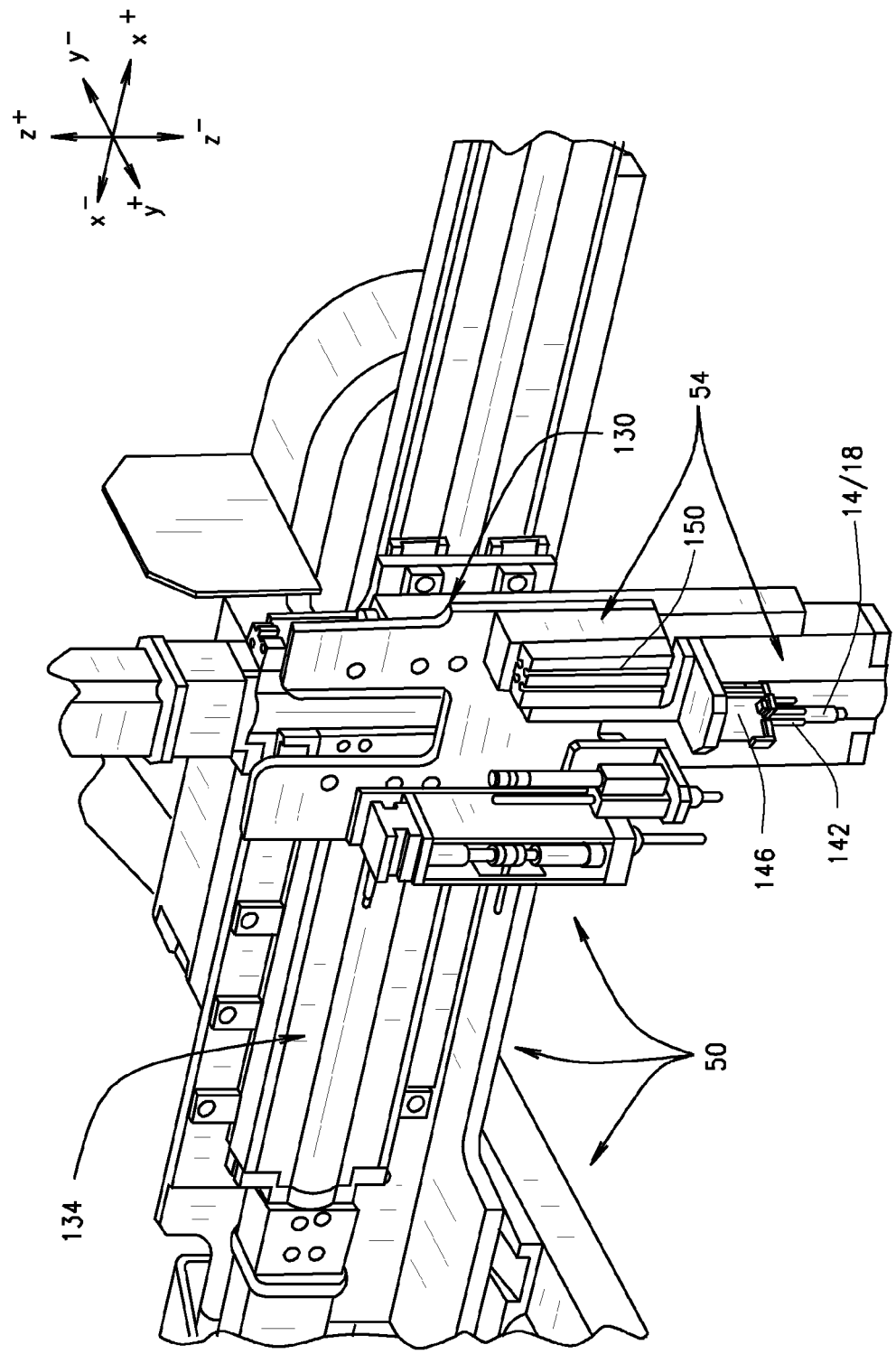
FIG. 4B is a partial view of an XYZ-axis robot of the work deck shown in FIG. 3A, in accordance with various embodiments of the present disclosure.
Figure 4C:
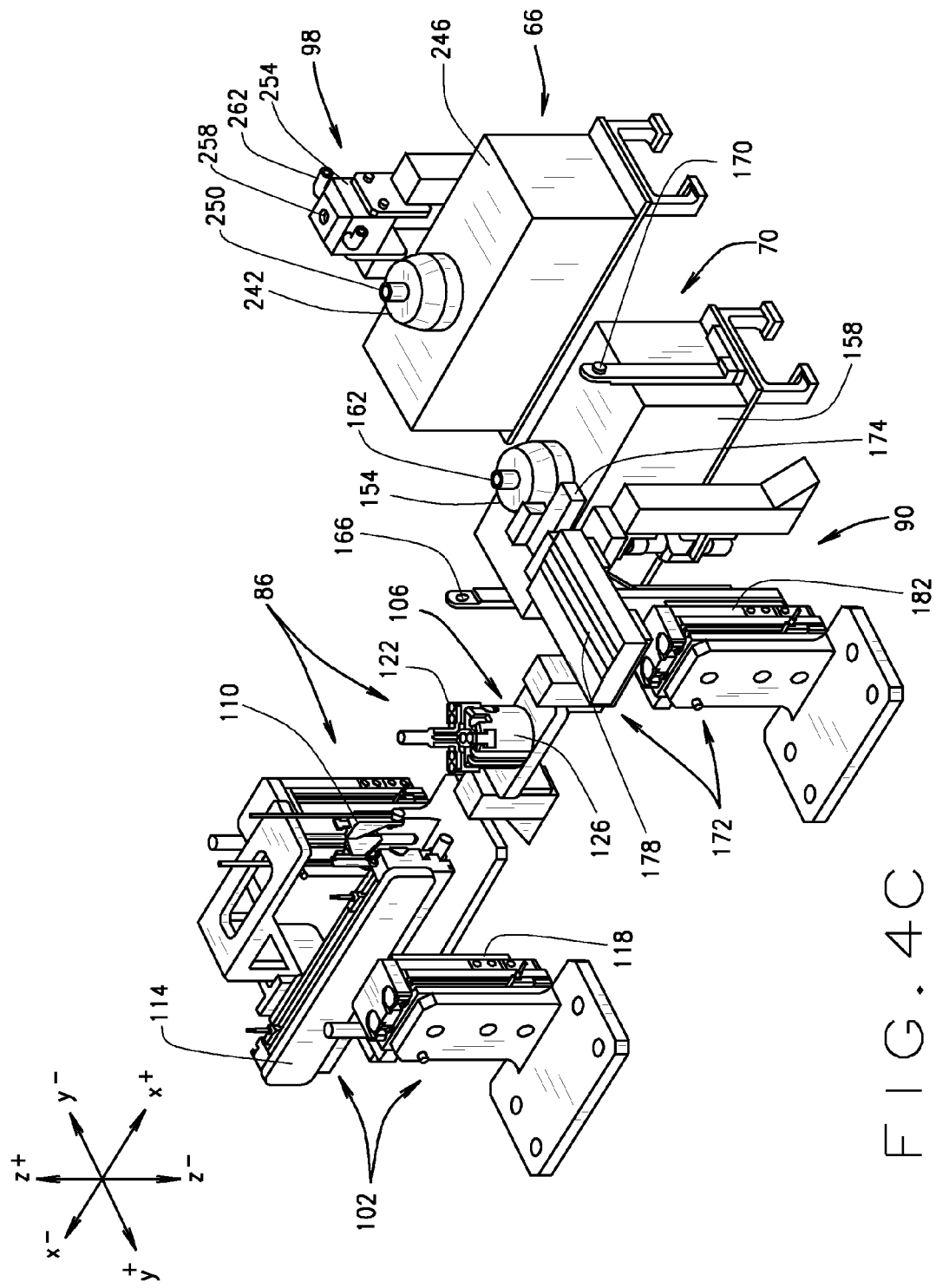
FIG. 4C is an isometric view of a capping and decapping station, a source tube balance, a pipette wiping station and a destination tube balance of the work deck shown in FIG. 3A, in accordance with various embodiments of the present disclosure.
Figure 4E:
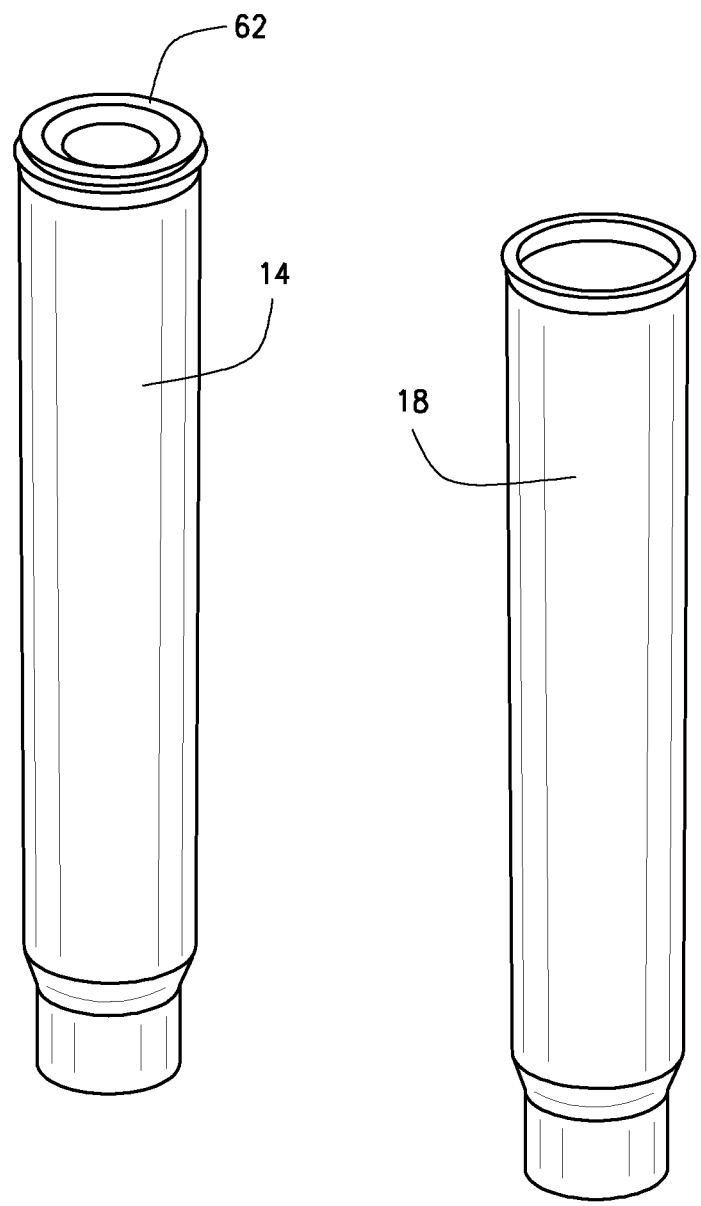
FIG. 4E is an isometric view of a source tube and a destination tube that are manipulated by the automated transfer and distribution system shown in FIGS. 1A and 1B, in accordance with various embodiments of the present disclosure.
Figure 5A:
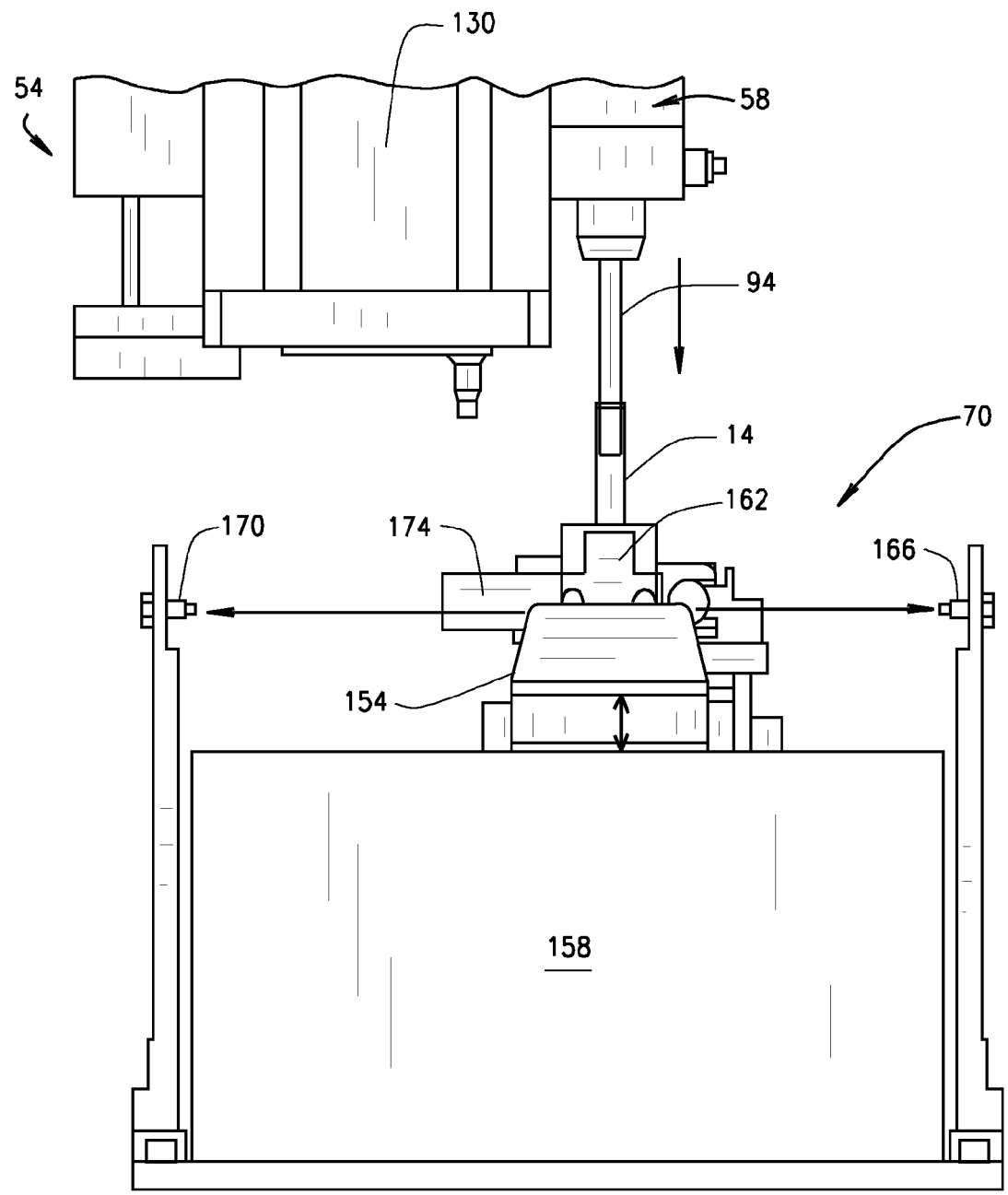
FIG. 5A is a side view of a source balance of the work deck shown in FIG. 3A, in accordance with various embodiments of the present disclosure.
Figure 5B:
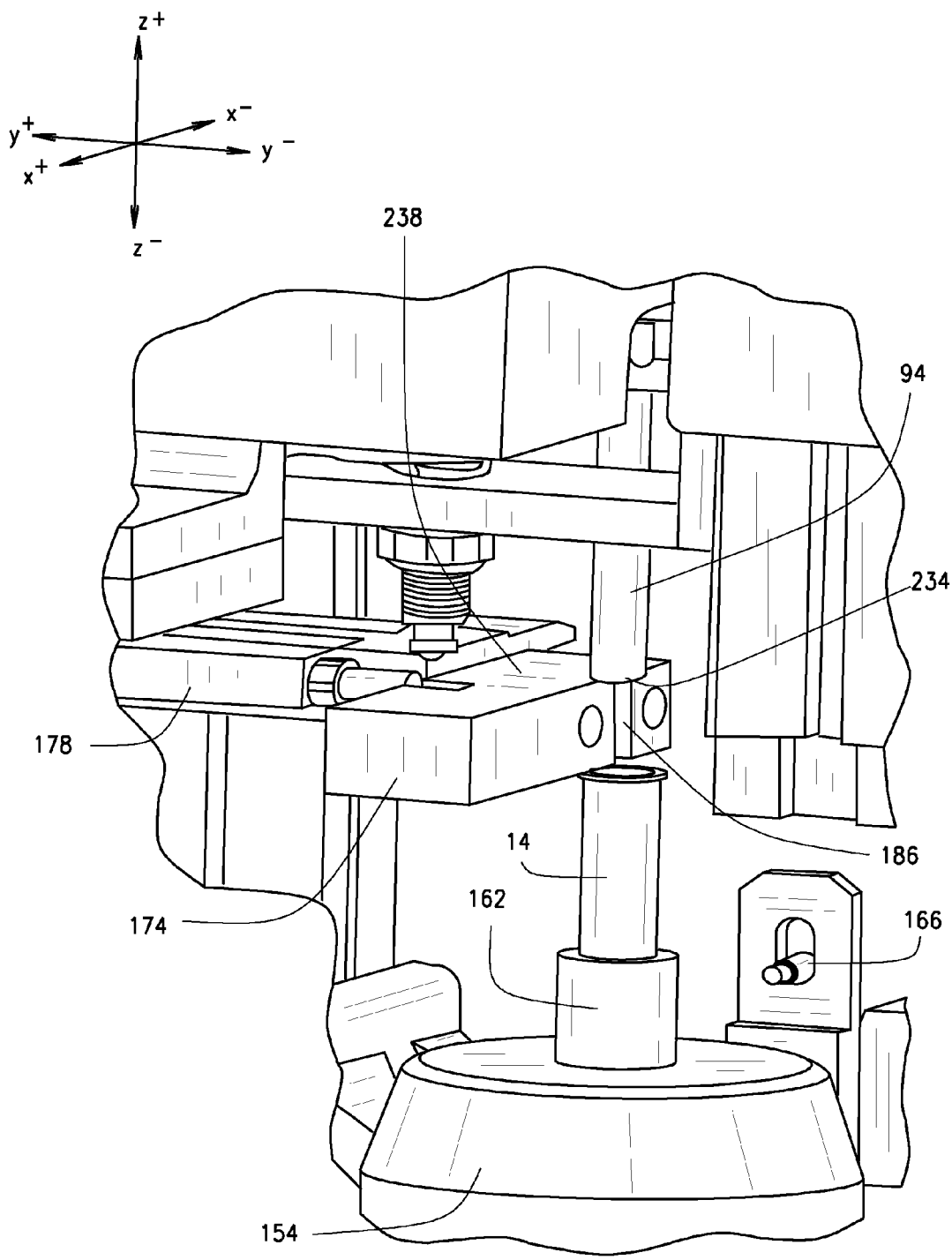
FIG. 5B is an isometric view of a pipette wiper of the work deck shown in FIG. 3A, in accordance with various embodiments of the present disclosure.

Referring now to FIGS. 4C, 5A and 5B, the source tube balance 70 includes the source tube balance head 154, a source tube load cell 158 to which the head 154 is connected via a biasing means, e.g., a calibrated spring. Particularly, the head 154 and load cell 158 are structured and cooperatively operable such that the source tube balance 70 provides a scale having a sensitivity capable of measuring very light weights, e.g., milligrams. Thus, when a source tube 14 containing seed is placed into the head 154, the weight of the seed (i.e., total weight of the seed plus the weight of the source tube 14, minus the known weight of the source tube 14) can be sensed by the source tube balance 70 and communicated to the control system 48 for storage in an electronic database or table of the control system 48. Moreover, after a specified amount of seed is aspirated, i.e., removed, from the source tube, as described below, the source tube balance 70 can provide a post-aspiration weight of the seed for verification that the correct amount of seed was in fact aspirated from the respective source tube 14.

The head 154 comprises a tube nest 162 that is sized and structured to receive and secure source tubes 14 within the head 154 during the weighing and aspiration processes. Additionally, the source tube balance 70 includes a pair of opposing optical sensors 166 and 170 that emit and receive an optical signal or beam that is monitored by the control system 48 to determine when the pipette nozzle 94 has contacted seed within the respective source tube 14, as described below. Particularly, one of the optical sensors, e.g., sensor 166, is signal transmitter that continuously emits an optical signal to the other optical sensor, e.g., sensor 170, which is a signal receiver that senses when the signal/beam is or is not being received.

As described above, the work deck 26 includes the pipette wiping (PW) device 90 that is structured and operable to remove excess seed from the tip of a pipette nozzle 94 after the seed has been aspirated from the respective source tube 14. More specifically, the PW device 90 removes excess seed from an exterior of the tip the pipette nozzle 94 and redeposits the wiped excess seed back into the respective source tube 14. The PW device 90 comprises a PW YZ-axis robot 172, referred to herein as the PW robot 172, that is structured and operable to move a wiper block 174 to and from a position over the top of each source tube 14 secured within the tube nest 162 after seed has been aspirated from the respective source tube 14. The PW robot 172 includes a PW Y-axis linear stage 178 for moving the wiper block 174 in the $Y^{+/-}$ directions and a PW Z-axis linear stage 182 for moving the wiper block in the $Z^{+/-}$ directions. The wiper block 174 comprises a seed channel 186 (shown best in FIG. 5B) that is structured and operable to guide wiped seed back into the respective source tube 14, as described below.

Figure 6:
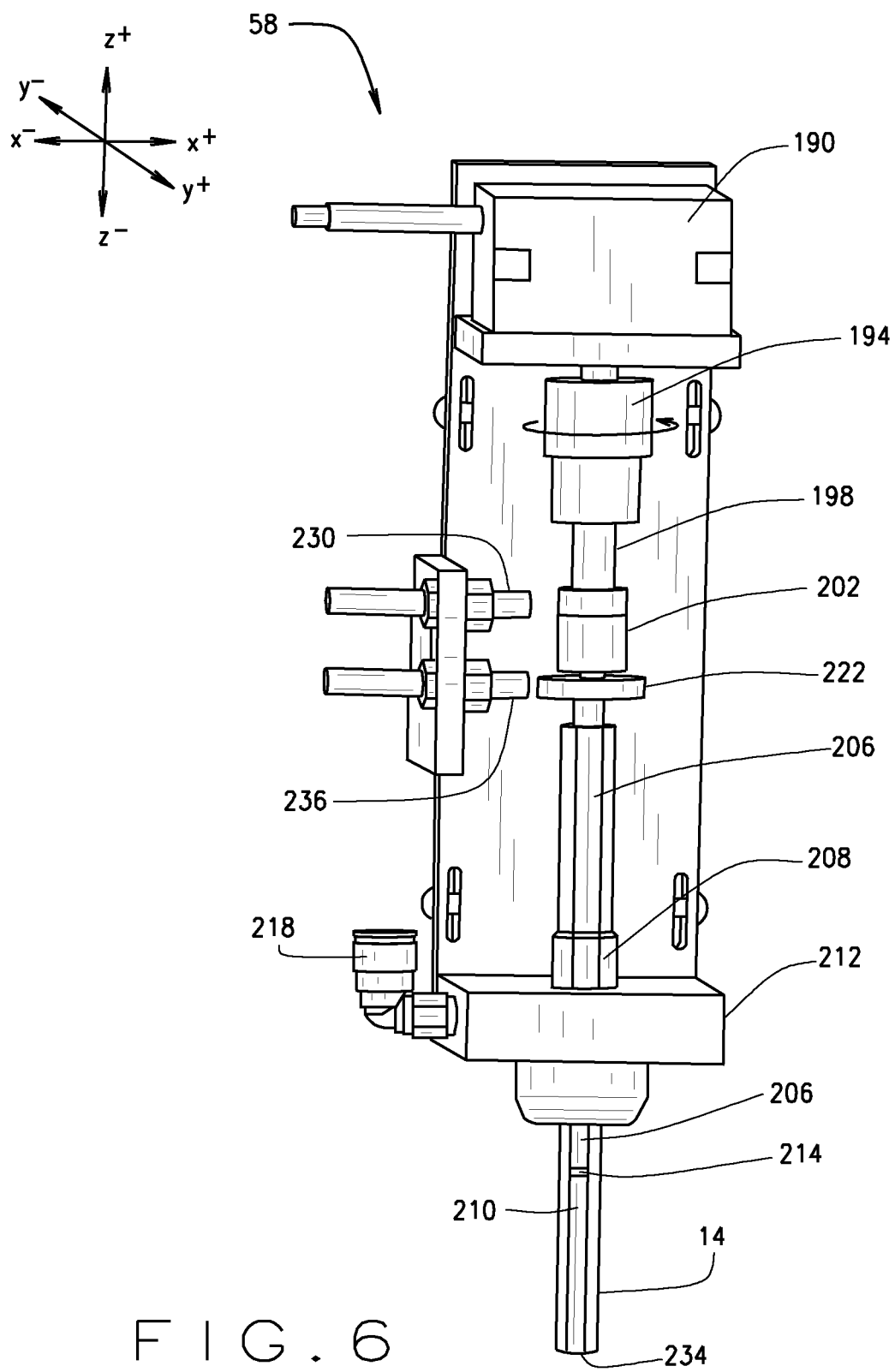
FIG. 6 is an isometric view of an automated volume adjustable pipette of the work deck shown in FIG. 3A, in accordance with various embodiments of the present disclosure.
Figure 7:
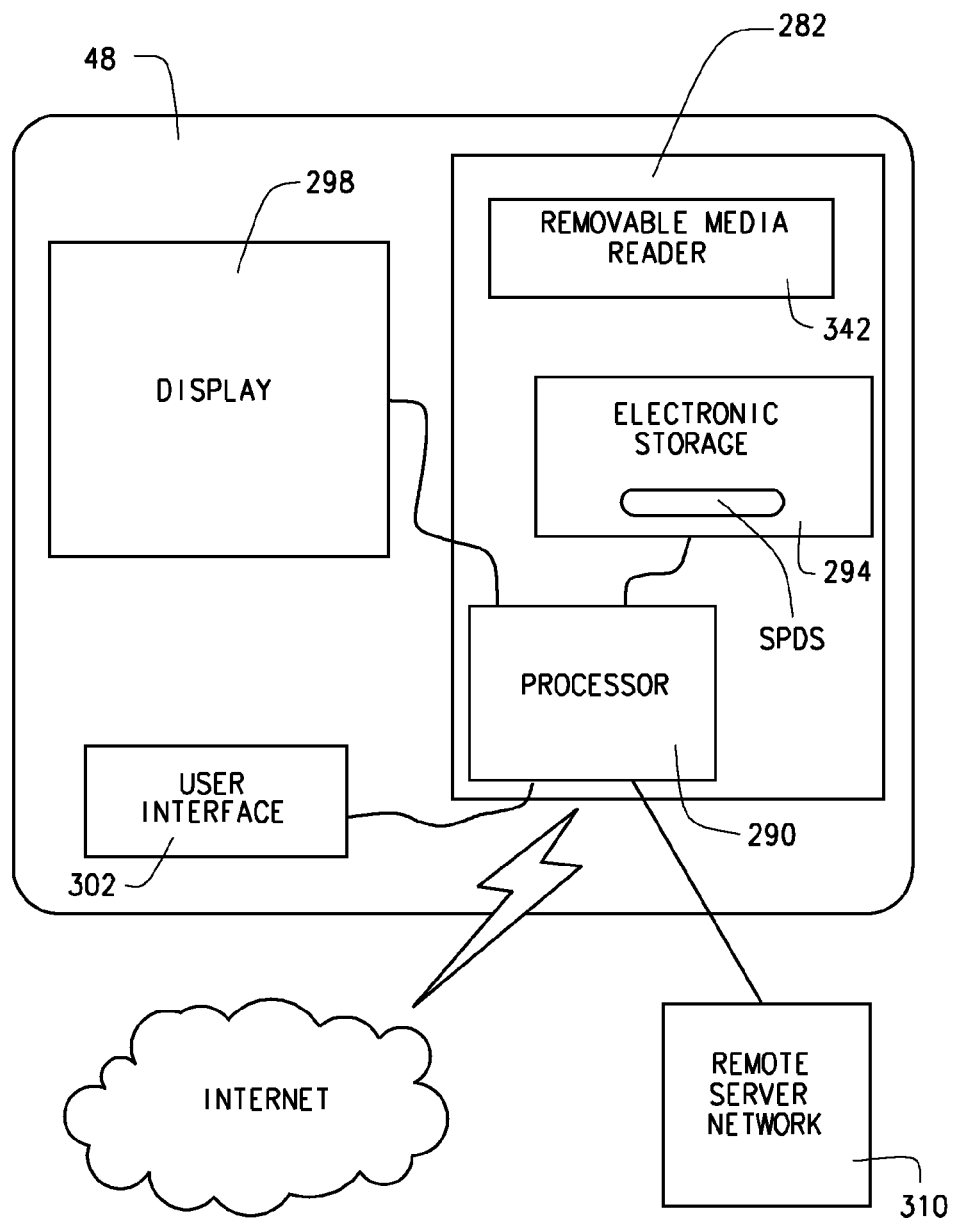
FIG. 7 is a block diagram of a central control system of the automated transfer and distribution system shown in FIGS. 1A and 1B, in accordance with various embodiments of the present disclosure.

Referring now to FIG. 6, as described above, the automated volume adjustable pipette 58 is structured and operable to aspirate, i.e., remove, selected amounts e.g., volumes and/or weight, of seed from the selected source tubes 14 and distribute, or dispose, the aspirated seed into a respective destination tube 18. More specifically, the pipette 58 is structured and operable to automatically adjust an internal volume of the pipette nozzle 94 such that automatically adjustable amount of seed can be aspirated from each respective source tube 14. The pipette 58 comprises a bi-directional stepper motor 190 that is connected to a collar 194 and is structured and operable to bi-directionally rotate the collar 194 as controlled by the control system 48. The pipette additionally includes a spline shaft 198 that is slidingly engaged with the collar 194 such that rotation of the motor 190 and the collar 194 will also rotate the spline 198. Additionally, the spline shaft 198 is slidingly engaged with the collar 194 such that the spline shaft 198 can freely translate in the $Z^{+/-}$ directions. The pipette 58 further includes a coupler 202 that fixedly connects the spline shaft 198 to a threaded rod 206 that extends into an internal bore 210 of the pipette nozzle 94 and is threadingly engaged with a threaded sleeve 208 that is fixedly connected to a bottom plate 212 of the pipette 58. A filter screen 214, e.g., a sintered stainless steel filter screen, is disposed at a distal end of the threaded rod 206 within the bore 210 and the bore 210 is fluidly connected with a vacuum and pressure connector 218 that is connectable to a vacuum source (not shown), and in various embodiments, with a pressure source (not shown). Furthermore, the pipette 58 includes a position sensor ring 222 disposed about a proximal end of the threaded rod 206, and a home position sensor 226 and limit position sensor 230 mounted to a frame of the pipette adjacent the position sensor ring 222.

Generally, as controlled by the control system 48, the stepper motor 190 will rotate the collar 194 a specified angular distance, e.g., 1° to 1080° or more, in a commanded direction, which in turn rotates the spline shaft 198, the coupler 202, the position sensor ring 222 and the threaded rod 206 the specified angular distance. As a consequence of the threaded engagement of the threaded rod 206 with the threaded sleeve 208, the rotation of the threaded shaft causes the threaded shaft and the filter 214 to move in the specified $Z^+$ or $Z^-$ direction. Particularly, the rotation causes the filter 214 to move in the $Z^{(+ \ or \ -)}$ direction within the nozzle bore 210 such that a specified volume within the bore 210 between the filter 214 and the tip 234 of the nozzle 94 is defined. The defined volume is substantially equal to a specified amount of seed that is to be aspirated from the respective source tube 14, as indicated in a database or table stored in the control system 48. Once the filter 214 has been controllably positioned within the nozzle bore 210, thereby defining a particular specified volume within the nozzle bore 210 between the filter 214 and the tip 234, the vacuum source can be activated to generate a vacuum within the bore 210. Consequently, when the nozzle 94 is positioned within the respective source tube 14, as described below, seed will be aspirated from the source tube 14 and drawn into the nozzle 94 until the controllably defined volume is full. Hence, the defined volume within the nozzle 94 can be controllably adjusted such that the amount of seed aspirated from each respective source tube 14 can be controllably adjusted and set from aspiration to aspiration.

Additionally, in various embodiments, the home and limit position sensors 226 and 230 read the position sensor ring to calibrate the $Z^+$ and $Z^-$ positions of the threaded rod 206 to accurately define the volume within the nozzle bore 210 between the filter 214 and the tip 234. Particularly, the home sensor 226 is utilized to position the position sensor ring 222, and hence the filter 214, in a home position from which the sensor ring 222 and filter 214 can be moved in the $Z^+$ and $Z^-$ directions to define the specified volume within the nozzle 94.

Referring now to FIGS. 4C, 5A, 5B and 6, in operation, after the cooperative operation of the work deck robot 50 and the tube handling device 54 removes the decapped source tube 14 from the clamp stand 106 and places the decapped source tube 14 into the head 154 of the source tube balance 70, more particularly into the tube nest 162, the cooperative operation of the work deck robot 50 and the automated pipette 58 begin to slowly insert the pipette nozzle 94 into the respective source tube 14. Specifically, the work deck robot 50 very slowly lowers the pipette nozzle 94 into the respective source tube 14 until the tip 234 of the nozzle 94 contacts the top of the seed within the respective source tube 14.

As described above, the source tube balance head 154 is connected to the source tube load cell 158 via a biasing device, such as a calibrated spring. The biasing means is structured and operable to apply a force in the $Z^+$ direction on the head 154 such that when the head 154 is in a static position there is space between a bottom of the head 154 and a top surface of the load cell 158. Additionally, the optical sensors 166 and 177 are positioned such that when the head 154 is in the static position, the emitted optical signal/beam is broken by the head 154, i.e., the head 154 prevents the transmitted signal/beam from being received by the receiving sensor 166 or 170. Specifically, the sensors 166 and 170 are positioned such that the emitted signal/beam hits the head 154 just below a top surface of the head 154, such that a very slight movement of the head 154 in the $Z^-$ direction will allow the emitted optical signal to be received by the receiving sensor 166 or 170.

As the nozzle 94 is continued to be lowered into the respective source tube 14 the tip 234 of the nozzle 94 will contact the seed, whereby the nozzle 94 will push the respective source tube 14 and the head 154 downward in the $Z^-$ direction allowing the emitted optical signal to be received by the receiving sensor 166 or 170. When the optical signal is received by the receiving sensor 166 or 170, the control system 48 knows that the pipette nozzle 94 has contacted the seed within the respective source tube 14 and commands the work deck robot 50 to cease lowering the pipette nozzle 94 within the respective source tube 14.

Prior to (or simultaneously with) lowering the nozzle 94, the pipette filter 214 is positioned within the pipette bore 210 to accurately define the volume within the nozzle bore 210 between the filter 214 and the tip 234, as described above. Subsequently, the control system 48 activates the vacuum source such that a vacuum is provided within the nozzle 94, whereby the pipette 58 aspirates the specified amount of seed from the respective source tube 14. Once the specified amount of seed has been aspirated from the respective source tube 14, the vacuum is continuously applied to retain the aspirated seed within the nozzle 94. The PW robot 172 then moves the wiper block 174 to a position over the top of the respective source tube 14 such that the seed channel 186 is aligned with the top opening for the respective source tube 14. Thereafter, the work deck robot 50 raises the pipette nozzle 94 in the $Z^+$ such that the tip 234 is substantially even with a top surface 238 of the wiper block 174. Subsequently, the work deck robot 50 slowly moves the pipette nozzle 94 in the $Y^+$ direction such that the wiper block top surface 238 wipes any excess seed protruding from or stuck to an exterior of the nozzle tip 234 from the tip 234. The wiped seed then falls, via gravity from the tip 234 and the seed channel guides the wiped seed back into the respective source tube 14.

Referring now to FIG. 4C, the destination tube balance 66 includes the destination tube balance head 242, a destination tube load cell 246 to which the head 242 is connected via a biasing means, e.g., a calibrated spring. Particularly, the head 242 and load cell 246 are structured and cooperatively operable such that the destination tube balance 66 provides a scale having a sensitivity capable of measuring very light weights, e.g., milligrams. Thus, when a destination tube 18 is placed into the head 242, the weight of the destination tube 18 can be sensed by the destination tube balance 66 and communicated to the control system 48 for storage in an electronic database or table of the control system 48. Moreover, after a specified amount of seed is deposited into the destination tube 18, as described below, the destination tube balance 66 can provide a post-deposition weight of the destination tube 18 plus the seed for verification that the correct amount of seed, i.e., approximately all the seed aspirated from the source tube 14, was in fact deposited into the respective destination tube 18. The head 242 comprises a tube nest 250 that is sized and structured to receive and secure destination tubes 18 within the head 242 during the deposition of the seed.

As described above, as the source tube cap 62 is being removed from a selected source tube 14, the work deck robot 50 selectively removes a destination tube 18 from the respective destination tube tray 42, based on the destination tube barcode identification that is pre-loaded into the SPDS software and places the selected destination tube 18 into a destination tube balance 66 of the work deck 26. More specifically, the work deck robot 50 places the selected destination tube 18 into the tube nest 250 of the destination tube balance head 242.

As described above, the work deck 26 further includes a pipette cleaning station 98 that is structured and operable to remove residual seed from the pipette nozzle 94 after seed is deposited into a destination tube 18. The pipette cleaning station 98 comprises a vacuum and pressure head 254 having a tube cup 258 defined therein that is fluidly connected to a vacuum and pressure connector 262 that is connectable to a vacuum and pressure source (not shown).

Referring now to FIGS. 3A, 3B, 3C, 4B, 4C and 6, in operation, once seed has been aspirated from a source tube 14 and the pipette nozzle tip 234 has been wiped, as described above, the control system 48 continuously provides a vacuum to the pipette nozzle 94 such that the specified amount aspirated seed is retained within the nozzle 94. Subsequently, the work deck robot 50 positions the pipette nozzle 94 above a selected destination tube 18 that has been placed in the destination tube balance nest 250, as described above. The work deck robot 50 then lowers the nozzle 94 in the $Z^-$ direction until the nozzle tip 234 is positioned within a top portion of the respective destination tube 18. Once the nozzle 94 is positioned within the respective destination tube 18, the control system 48 ceases application of the vacuum to the nozzle 94 such that the aspirated seed falls, via gravity, into the respective destination tube 18. In various embodiments, once the aspirated seed is allowed to fall into the respective destination tube 18, the control system 48 applies a slight blowing pressure, via the pressure source connected to the vacuum and pressure connector 218 of the pipette 58, to gently blow the aspirated seed from within the nozzle 94 such that the seed is deposited into the respective destination tube 18.

Once the seed has been deposited into the respective destination tube 18, the work deck robot 50 removes the pipette nozzle 94 from the destination tube 18 and then moves the nozzle 94 to a position above the pipette cleaning station tube cup 258. The work deck robot then lowers the pipette nozzle 94 in the $Z^-$ direction such that the tip 234 of the nozzle 94 is disposed within the tube cup 258. Subsequently, the control system 48 applies a slight blowing pressure, via the pressure source connected to the vacuum and pressure connector 218 of the pipette 58, to gently blow out any residual seed remaining in within the nozzle bore 210, and/or the control system 48 generates a vacuum within the tube cup 258, via the vacuum source connected to the vacuum and pressure connector 262 of the pipette cleaning station 98, to gently vacuum any residual seed remaining in within the nozzle bore 210. Additionally, in various embodiments, the control system 48 generates a blowing pressure within the tube cup 258, via the vacuum and pressure source connected to the vacuum and pressure connector 262 of the pipette cleaning station 98, to remove any residual seed attached to exterior of the pipette nozzle 94.

As described above, the application of the blowing pressure and/or the vacuum pressure(s) remove(s) any residual seed from within the nozzle bore 210 and from the exterior of the pipette nozzle 94, thereby providing a clean nozzle 94 for subsequent aspirations from subsequent source tubes 14 and, importantly, preventing any cross-contamination of seed deposited into subsequent destination tubes 18.

Additionally, after the seed has been deposited into the destination tube 18, the resulting weight of the filled destination tube 18 is measured via the destination tube balance 66. The post-deposition change in weight of the destination tube 18 is then compared to the post-aspiration weight of the respective source tube 14 by the control system 48 to verify that specified amount of seed was aspirated from the source tube 14 and deposited into the destination tube 18.

After the pipette nozzle 94 has been cleaned at the cleaning station 98, as described above, the work deck robot 50 removes the respective source tube 14 from the source tube balance tube nest 162 and places the source tube 14 into the source tube clamp stand 106 of the C&D station 86 where the clamp fingers 122 are actuated to retain the source tube 14 within the clamp stand 106. The C&D robot 102 then positions the previously removed tube cap 62, still being retained by the cap gripper 110, over the source tube 14, and the cooperative operation of the C&D robot 102 and the cap gripper 110 replace the tube cap 62 onto, or into, the respective source tube 14.

As the tube cap 62 is being replaced onto, or into, the source tube 14, the work deck robot 50 removes the filled destination tube 18 having the deposited seed therein from the destination tube balance tube nest 250, transports the filled destination tube 18 back to the tray dock 46 and reinserts the filled destination tube 18 into the respective destination tube tray 42. Subsequently, the work deck robot 50 retrieves the recapped source tube 14 from the clamp stand 106, transports the recapped source tube 14 back to the tray dock 46 and reinserts the recapped source tube 14 into the respective well of the respective source tube tray 38 from which the source tube 14 was initially removed.

Thereafter, the automated small particle distribution system 10, as controlled by the control system 48, repeatedly removes source and destination tubes 14 and 18 from the source and destination trays 38 and 42, decaps the source tubes 14, aspirates seeds from the source tubes 14, deposits the aspirated seed into the destination tubes 18, and returns the respective source and destination tubes 14 and 18 to their respective wells within their respective source and destination trays 38 and 42, as described above, until all the specified seed (as controlled by the control system 48) is aspirated from the source tubes 14 of the source tube trays 38 that have been placed in the tray docks 46. Further thereafter, the 6-axis robot arm 30 removes the source tube trays 38 and/or the destination tube tray(s) 42 from the tray docs 46 and replaces the trays 38 and/or 42 back into the respective tray receptacles 36 of the storage carousel 34. Subsequently, as controlled by the control system 48, the 6-axis robot arm 30 removes other source tube trays 38 and/or destination tube trays 42 from the storage carousel 34, and the process is repeated until all the specified seed from all the specified the source tubes 14 of the storage carousel 34 have been deposited into destination tubes 18, as described above.

Referring now to FIGS. 1A, 2A, 2B and 7, as described above, the system 10 is controlled by the central control system 48, more particularly, by execution of the SPDS software by a processor of the control system 48. As illustrated in FIGS. 1A and 2A, in various embodiments, the control system 48 includes various computers and electrical modules or panels that are located beneath the loading deck 22 and/or the work deck 26. More particularly, in various embodiments, the control system 48 is a computer based system that generally includes one or more computers 282 and one or more electrical modules, or panels, 286. Each computer 282 includes at least one processor 290 suitable to execute at least a portion of the SPDS software to control all functions of central control system 48 to automatically, or robotically, control the operation of the system 10, as described herein. Each computer 282 additionally includes at least one electronic storage device 294 that comprises a computer readable medium, such as a hard drive or any other electronic data storage device for storing such things as the SPDS software, algorithms and digital information, data, look-up tables, spreadsheets and databases. Furthermore, the control system 48 includes a display 298 for displaying such things as information, data and/or graphical representations, and at least one user interface device 302, such as a keyboard, mouse, stylus, and/or an interactive touch-screen on the display 298. In various embodiments each computer 282 can include a removable media reader 306 for reading information and data from and/or writing information and data to removable electronic storage media such as floppy disks, compact disks, DVD disks, zip disks, flash drives or any other computer readable removable and portable electronic storage media. In various embodiments the removable media reader 282 can be an I/O port of the respective computer 282 utilized to read external or peripheral memory devices such as flash drives or external hard drives.

In various embodiments, the control system 48, e.g., one or more of the computers 282, can be communicatively connectable to a remote server network 310, e.g., a local area network (LAN), via a wired or wireless link. Accordingly, the control system 48 can communicate with the remote server network 310 to upload and/or download data, information, algorithms, software programs, and/or receive operational commands. Additionally, in various embodiments, the control system 48 can be structured and operable to access the Internet to upload and/or download data, information, algorithms, software programs, etc., to and from Internet sites and network servers.

Referring now to FIGS. 1A and 1B, as described above, the system 10 includes the environmentally and static controlled system enclosure 28 that fully encloses the loading deck 22 and the work deck 26. In various embodiments, the enclosure 28 is humidity controlled and includes guarded fiberglass panels 266 and at least one access door 270. In various implementations, the access door(s) 270 can include safety interlocks 274. It is further envisioned that in various embodiments, the system 10 can includes one or more emergency stop (e-stop) buttons 278 that are operable to instantly shut down all operation of the system 10.

Thus, the seed distribution automation system 10, as described above, can be utilized to facilitate, inter alia, a seed screening process by providing higher accuracy, consistency in the transfer of seed from source tubes 14 to destination tubes 18, elimination of cross-contamination issues, higher throughput, and alleviation of ergonomic issues associated with a manual process.

The description herein is merely exemplary in nature and, thus, variations that do not depart from the gist of that which is described are intended to be within the scope of the teachings. Such variations are not to be regarded as a departure from the spirit and scope of the teachings.

What is claimed is:

1. An automated small particle distribution system for transferring small particles from source tubes to destination tubes, said system comprising:

a loading deck structured and operable to store and provide a plurality of source tube trays and a plurality of destination tube trays, each source tube tray having a plurality of source tubes stored therein, and each destination tube tray having a plurality of destination tubes stored therein, the loading deck comprising:
 a storage carousel structured and operable to retain the source tube trays and the destination tube trays, each source tube tray having the plurality of source tubes stored therein, and each destination tube tray having the plurality of destination tubes stored therein: and
 a 6-axis robot arm structured and operable to:
  remove selected source tube trays and selected destination tube trays from the storage carousel and place the removed source and destination tube trays on tray docks of the work deck, and
  return the selected source tube trays and destination tube trays from the tray docks to the storage carousel; and a work deck structured and operable to:
  receive selected source tube trays and selected destination tube trays from the loading deck,
  aspirate various specified amounts of small objects stored in selected source tubes, and
  deposit the aspirated small objects into selected destination tubes without cross-contamination of small objects,
  the work deck comprising an XYZ-axis robot structured and operable to move selected source and destination tubes, one at a time, from the selected source tube and destination tube trays to various locations of the work deck to aspirate the specified amounts of small objects from the selected source tubes and deposit the aspirated small objects into the selected destination tubes.

2. The system of claim 1, wherein the work deck further comprises a capping and decapping station structured and operable to remove a respective cap from each of respective source tubes prior to aspiration of the small objects and replace the respective cap post aspiration of the small objects.

3. The system of claim 1, wherein the work deck further comprises a source tube balance structured and operable to:
  weigh each respective source tube prior to aspiration,
  retain each respective source tube during aspiration, and
  weigh each respective source tube post aspiration.

4. The system of claim 1, wherein the work deck further comprises an automated volume adjustable pipette mounted to the XYZ-axis robot that is structured and operable to:
  automatically adjust a volume within a bore of a nozzle of the pipette to aspirate a specified amount of small objects from each respective source tube, the specified amount of small objects to be aspirated specific to each respective source tube and variable from one source tube to a subsequent source tube, and
  deposit each specified amount of aspirated small objects into a respective one of the destination tubes.

5. The system of claim 4, wherein the work deck further comprises a pipette wiping device including a seed channel, the pipette wiping device structured and operable to:
  remove excess small objects from a tip of the pipette nozzle after the specified amount of small objects has been aspirated from each respective source tube; and
  guide the wiped seed back into each respective source tube, via the seed channel.

6. The system of claim 4, wherein the work deck further comprises a destination tube balance structured and operable to:
  weigh each respective destination tube prior to each specified amount of aspirated small objects being deposited into each respective destination tube,
  retain each respective destination tube during deposition, and
  weigh each respective destination tube after each specified amount of aspirated small objects is deposited into each respective destination tube.

7. The system of claim 4, wherein the work deck further comprises a pipette cleaning station structured and operable to remove residual small objects from at least one of an interior of the nozzle bore and an exterior of the nozzle after deposition of each specified amount of small objects into each respective destination tube.

8. The system of claim 1 further comprising an environmentally controlled system enclosure structured and operable to enclose the loading deck and the work deck.

9. The system of claim 1, wherein the small object are seeds.

10. A method for transferring small particles from source tubes to destination tubes, said method comprising:
  storing and providing, via a loading deck of an automated small particle distribution system, a plurality of source tube trays and a plurality of destination tube trays, each source tube tray having a plurality of source tubes stored therein, and each destination tube tray having a plurality of destination tubes stored therein, the source tube trays and the destination tube trays retained in a storage carousal of the loading deck;
  removing selected source tube trays and selected destination tube trays from the storage carousel and placing the removed source and destination tube trays on tray docks of a work deck of the automated small particle distribution system, via a 6-axis robot arm of the loading deck;
  aspirating various specified amounts of small objects stored in selected source tubes, via the work deck of the automated small particle distribution system;
  depositing the aspirated small objects into selected destination tubes without cross-contamination of small objects, via the work deck of the automated small particle distribution system;
  moving, via an XYZ-axis robot of the work deck, selected source and destination tubes, one at a time, from the selected source tube and destination tube trays to various locations of the work deck to aspirate the specified amounts of small objects from the selected source tubes and deposit the aspirated small objects into the selected destination tubes; and
  returning the selected source tube trays and destination tube trays from the tray docks to the storage carousel, via the 6-axis robot arm.

11. The method of claim 10 further comprising removing a respective cap from each of respective source tubes prior to aspiration of the small objects and replacing the respective cap post aspiration of the small objects, via a capping and decapping station of the work deck.

12. The method of claim 10 further comprising:
  weighing each respective source tube prior to aspiration, via a source tube balance of the work deck,
  retaining each respective source tube during aspiration, via the source tube balance, and
  weighing each respective source tube post aspiration, via the source tube balance.

13. The method of claim 10 further comprising:
  automatically adjusting a volume within a bore of a nozzle of an automated volume adjustable pipette of the work deck to aspirate a specified amount of small objects from each respective source tube, the specified amount of small objects to be aspirated specific to each respective source tube and variable from one source tube to a subsequent source tube, and
  depositing each specified amount of aspirated small objects into a respective one of the destination tubes, via the adjustable pipette.

14. The method of claim 13 further comprising:
  removing excess small objects from a tip of the pipette nozzle after the specified amount of small objects has been aspirated from each respective source tube, via a pipette wiping device of the work deck; and
  guiding the wiped seed back into each respective source tube, via a seed channel of the pipette wiping device.

15. The method of claim 13 further comprising:
weighing each respective destination tube prior to each specified amount of aspirated small objects being deposited into each respective destination tube, via a destination tube balance of the work deck,
retaining each respective destination tube during deposition, via the destination tube balance, and
weighing each respective destination tube after each specified amount of aspirated small objects is deposited into each respective destination tube, via the destination tube balance.

16. The method of claim 13 further comprising removing, via a pipette cleaning station of the work deck, residual small objects from at least one of an interior of the nozzle bore and an exterior of the nozzle after deposition of each specified amount of small objects into each respective destination tube.

* * * * *